United States Patent [19]

Cooper

[11] Patent Number: 4,599,359

[45] Date of Patent: Jul. 8, 1986

[54] HYDROXYZINE-CONTAINING ANALGESIC COMBINATIONS

[75] Inventor: Stephen A. Cooper, 85 Westview Rd., Short Hills, N.J. 07078

[73] Assignee: Stephen A. Cooper, Short Hills, N.J.

[21] Appl. No.: 668,896

[22] Filed: Nov. 7, 1984

Related U.S. Application Data

[63] Continuation-in-part of Ser. No. 586,566, Mar. 6, 1984, abandoned, which is a continuation-in-part of Ser. No. 448,290, Dec. 9, 1982, abandoned.

[51] Int. Cl.$^4$ .............................................. A61K 31/19
[52] U.S. Cl. .................................................... 514/557
[58] Field of Search .......................... 424/317; 514/557

[56] References Cited

U.S. PATENT DOCUMENTS

| | | | |
|---|---|---|---|
| 4,233,314 | 11/1980 | Gardocki | 424/317 |
| 4,233,315 | 11/1980 | Gardocki | 424/317 |
| 4,233,316 | 11/1980 | Gardocki | 424/317 |
| 4,233,317 | 11/1980 | Gardocki | 424/317 |

OTHER PUBLICATIONS

Merck Index, 9th Ed. (1976) p. 649.
Bluhm et al., Life Sciences, vol. 31, pp. 1229–1232 (1982).
Stambaugh et al, Adv. in Pain Research & Therapy, vol. I, Raven Pr., 1976, pp. 554–565.
Malkasian et al, Obstetrics & Gynecology, vol. 30, No. 4, Oct. 1967, pp. 568–575.
Benson et al, Am. J. Obst. & Gynec. 84:37–43, Jul. 1962.
Brelje et al., Obstetrics & Gynecology, vol. 27, No. 3, Mar. 1966, pp. 350–354.
Beaver et al, Adv. in Pain Research & Therapy, vol. 1, Raven Press, NY (1976) pp. 553–557.
Kantor et al., Adv. in Pain Research & Therapy, vol. 1, Raven Press, NY (1976) pp. 567–572.
Stambaugh, J. Clin. Pharm. 21, 295S–298 (1981).
Stambaugh, Del. Med. Jrl. 53, No. 2, Feb. 1981, 95–99.
Bellville et al, J. Clin. Pharmacology–May–Jun. 1979, pp. 290–296.
Basak, Curr. Therapeutic Research, vol. 29, No. 1, Jan 1981, pp. 12–16.
Hupert et al., Anesthesia & Analgesic, vol. 59, No. 9 (1980) pp. 690–696.
Takahashi et al, Shika Gaho 74(7): 1160–1166 (1974).
Monrose, Iryo 25(3): 181–188 (1971).
Physician's Desk Reference, 30th Ed. (1982) p. 1511.
Diamond et al., ASA Abstracts, A286, Anesthesiology, vol. 55, No. 3.

*Primary Examiner*—Stanley J. Friedman
*Attorney, Agent, or Firm*—Gerald D. Sharkin; Richard E. Vila

[57] ABSTRACT

Hydroxyzine or it's therapeutically acceptable, non-toxic salts, in combination with a non-steroidal, anti-inflammatory agent are effective analgesic compositions.

34 Claims, No Drawings

HYDROXYZINE-CONTAINING ANALGESIC COMBINATIONS

This application is a continuation-in-part of Application Ser. No. 586,566 filed Mar. 6, 1984 which in turn is a continuation-in-part of Ser. No. 448,290, filed Dec. 9, 1982, now both abandoned.

The present invention relates to analgesic compositions and more particularly to new analgesic combinations comprising 1-(p-chlorobenzhydryl)-4-[2-(2-hydroxyethoxy)ethyl]diethylenediamine or a therapeutically acceptable, non-toxic organic acid or a mineral acid addition salt thereof in combination with at least one non-steroidal, anti-inflammatory agent. The present invention also relates to a method for alleviating pain using the aforementioned analgesic combinations.

BACKGROUND OF THE INVENTION

Non-steroidal anti-inflammatory agents represent a well known class of pharmaceutical agents commonly referred to as NSAIDs. Such agents exhibit anti-inflammatory, analgesic and anti-pyretic activity and typically have other biological effects in humans, such as platelet aggregation inhibition activity. The NSAIDs also characteristically inhibit the synthesis of prostaglandins in well known in vitro assays. The NSAIDs provide more or less moderate non-narcotic analgesia and are typically used to alleviate mild to moderate pain, both chronic and acute, in a wide variety of situations. The NSAIDs are also characterized, more or less, by certain undesired or side effects, e.g. ulcerogenic effects, which are usually mainly of concern when administered at high doses and/or over long time periods, but side effects are judged of far less concern than with the stronger, narcotic analgesics.

The compound 1-(p-chlorobenzhydryl)-4-[2-(2-hydroxyethoxy)ethyl]-diethylenediamine (referred to generically as hydroxyzine) and its salt derivatives are known to be effective tranquilizers (see U.S. Pat. No. 2,899,436).

The search for analgesic agents of all kinds which will optimize the therapeutic effect and minimize undesired effects has been a long continuing quest in the attempt to find improved treatments. This search has included co-administrations involving analgesics, one with another or with a drug of another type. Among the wide variety of combined administrations which have been considered are those involving a tranquilizer and an analgesic. Such combinations have been mainly of interest in situations where both stress and great pain are anticipated or experienced, such as in surgical situations and the advanced stages of diseases such as cancer. For example, the literature reveals a number of clinical evaluations of the combination of hydroxyzine and a narcotic analgesic, generally co-administered by the i.v. or intramuscular routes, but the results in terms of analgesia have been largely judged to be additive.

SUMMARY OF THE INVENTION

It has now surprisingly been found that co-administration of hydroxyzine and acid salts thereof with one or more non-steroidal anti-inflammatory/analgesic agents (NSAIDs) has an especially advantageous effect in alleviating pain in human subjects. The invention is practised by administration adapted to achieve absorption through the alimentary canal, i.e. by oral or rectal administration, desirably by oral administration. The invention also provides pharmaceutical compositions for oral or rectal administration comprising: (a) one or more non-steroidal anti-inflammatory/analgesic agents, (b) hydroxyzine in free base form or in pharmaceutically acceptable acid addition salt form, and (c) a pharmaceutically acceptable carrier.

DETAILED DESCRIPTION OF THE INVENTION

In accordance with the present invention, pain is relieved in human subjects by co-administering thereto orally or rectally; (a) one or more non-steroidal anti-inflammatory/analgesic agents, and (b) hydroxyzine or an acid salt form thereof in an amount sufficient to potentiate the analgesic action of component (a); the total amount of components (a) and (b) being an amount sufficient to relieve pain.

Pharmaceutical compositions which are also provided by the present invention are adapted for oral or rectal administration and comprise a pain relieving effective amount of the combination of: (a) one or more non-steroidal anti-inflammatory/analgesic agents, (b) hydroxyzine or an acid salt form thereof in an amount sufficient to potentiate the analgesic action of component (a), and (c) a pharmaceutically acceptable carrier.

The amounts of hydroxyzine per dose to be employed in practicing the invention may be similar to those conventionally employed in using hydroxyzine as a tranquilizer, and generally will not exceed about 120 milligrams. At such levels my clinical investigations confirm that hydroxyzine is essentially inactive orally as an analgesic. Hence, the action of hydoxyzine in the present invention has been surprisingly found to be a synergism of the potentiating type. Preferably, the amount of hydroxyzine will not exceed 100 mg. per dose. In general, at least about 25 milligrams of hydroxyzine and its acid salts will be administered per dose in order to potentiate the analgesic effect of the NSAID. Preferably, at least 50 mg. and typically at least about 70 mg. of hydroxyzine will be administered per dose. Hence, a dose range for each administration of hydroxyzine and its salts may be from 25 mg. to 120 mg., more usually 25 mg. to 100 mg., preferably 50 mg. to 100 mg. and typically 70 mg. to 100 mg. The weighted dose amounts of hydroxyzine and its salts as referred to herein are on the equivalent basis of hydroxyzine dihydrochloride. It is generally preferred to employ the hydroxyzine in acid addition salt form, e.g. the dihydrochloride or pamoate.

Any of a wide variety of non-steroidal, anti-inflammatory agents may be used as active agents(a). Such materials include, by way of illustration only, aspirin; sodium 5-(4-chlorobenzoyl)-1,4-dimethyl-1H-pyrrole-2-acetate dihydrate (generically referred to as zomepirac sodium); 4-hydroxy-2-methyl-N-(2-pyridyl-2H-1,2-benzothiazine-3-carboxamide-1,1-dioxide (generic name Piroxicam); 2',4'-difluoro-4-hydroxy-3-biphenylcarboxylic acid (generic name Diflunisal); 1-isopropyl-7- methyl-4-phenyl-2(1H)-quinazolinone (generic name Proquazone); and arylacetic acid or arylpropionic acid compounds including the non-toxic therapeutically acceptable salts thereof, e.g. the sodium, potassium or calcium salts. Examples of useful arylacetic acid and arylpropionic acid compounds include 2-(p-isobutylphenyl)propionic acid (generic name Ibuprofen); alpha-methyl-4-(2-thienylcarbonyl) benzene acetic acid (generic name Suprofen); 4,5-diphenyl-2-oxazole propionic acid (generic name Oxaprozin); rac-6-chloro-alpha-methyl-carbazole-2-acetic acid (generic name Carprofen); 2-(3-phenyloxyphenyl)-propionic acid, particularly the calcium salt dihydrate thereof (these compounds being referred to generically as Fenoprofen and Fenoprofen calcium); 2-(6-methoxy-2-naphthyl) propionic acid (generic name Naproxen; the generic name of the sodium salt is Naproxen sodium); 4-(1,3-dihydro-1-oxo-2H-isoindol-2-yl)-α-methylbenzene acetic acid (generic name Indoprofen); 2-(3-benzoylphenyl) propionic acid (generic name Ketoprofen); and 2-(2-fluoro-4-biphenylyl) propionic acid (generic name Flurbiprofen) and 1-5-(4-Methylbenzoyl)-1H-pyrrole-2-acetic acid (generic name Tolmetin). All of the aforementioned non-steroidal, anti-inflammatory agents and their preparation are known. For example the synthesis of zomeriprac sodium, fenoprofen, indoprofen and ibuprofen is described in U.S. Pat. No. 4,242,519, U.S. Pat. No. 3,752,826, U.S. Pat No. 3,228,831 and U.S. Pat. No. 3,385,886, respectively.

The precise therapeutic dose of the individual components as well as the instantly disclosed combinations thereof may vary with the kind of pharmaceutic process, severity of the condition, administration schedule and other known factors, and doses typically continued until the condition causing the pain is ameliorated. With regard to the NSAID, it will be co-administered with a pain relieving potentiating effective amount of hydroxyzine (or its acid salts), in a total combined pain relieving effective amount, in doses given 1 to 6 times a day as needed to relieve pain. In general, it is desirable to employ at least an amount of the NSAID that would by itself be minimally effective clinically in the adult human to produce analgesia. The particularly preferred NSAIDs are those classed as arylacetic and arylpropionic acids (and their pharmaceutically acceptable salts) including, for example, ibuprofen, oxaprozin, carprofen, fenoprofen or fenoprofen calcium, naproxen or naproxen sodium, indoprofen, ketoprofen, flurbiprofen and tolmetin or tolmetin sodium. Also of particular interest are the NSAIDs proquazone, zomepirac, piroxicam and diflunisal.

The usefulness of the combinations of the present invention and the ability of hydroxyzine to potentiate the pain relieving properties of NSAID have been demonstrated in the following representative clinical trials in humans.

A clinical test was conducted involving subjects who were periodontal patients. After surgery was completed, the patients were given one dose of a medication and a questionnaire. They were asked to take the medication when their post-operative pain reached moderate to severe intensity. They were instructed to record their starting pain level, in numerical fashion, i.e., moderate (2) or severe (3), and then at 30 minutes and at each hour for the next four hours to record their pain intensity as severe (3), moderate (2), slight (1), or none (0); and their relief from the starting pain as complete (4), a lot (3), some (2), a little (1) or none (0). The procedure employed is state-of-the-art methodology and is described in more detail in an article entitled "A Model to Evaluate Mild Analgesics in Oral Surgery Outpatients", S. A. Cooper and W. T. Beaver, Clinical Pharmacology and Therapeutics, Vol., 20, Number 2, pp. 241–250, August, 1976.

In the test, the patients were given either 400 milligrams of ibuprofen, 100 milligrams of Hydroxyzine pamoate, or a mixture of 100 milligrams of Hydroxyzine pamoate and 400 milligrams of ibuprofen. The results of the test are recorded in Table 1 below. Pain intensity difference scores were derived by subtracting the pain level at 30 minutes and each hour after ingestion from the intensity at the time of initial administration. Hence, if the patient's pain was judged to be "moderate" (value of 2) at the start of the test and the patient judged his pain to be "slight" at 30 minutes and at hours one, two, three and four (assigned value of 1), the pain intensity difference score would be 5, that is 2 minus 1 or plus 1 at each of the five measuring points. Pain relief scores for each pain estimate were assigned according to patient's recorded estimate of relief. Accordingly, if the patient recorded a little relief at 30 minutes (a score of 1), some relief at hour two (a score of 2) and a lot of relief at hours three and four (score 3 for each hour) his pain relief score would be 9.

TABLE 1

|  | Hydroxyzine Pamoate 100 mg | Ibuprofen 400 mg | Combined |
|---|---|---|---|
| Number of Patients | 12 | 13 | 11 |
| Mean Sum Pain Intensity Difference Score | 0.33 | 6.69 | 7.73 |
| Mean Sum Pain Relief Score | 2.17 | 13.54 | 14.73 |
| Pain Intensity Difference at fourth hour. | 0.08 | 1.39 | 2.09 |
| Mean Pain Relief at fourth hour | 0.50 | 2.77 | 3.73 |

The data obtained from this first test when plotted showed at the end of 4 hours that the line of the curve for the combination was continuing essentially horizontally whereas the line for Ibuprofen alone was declining at an angle of about 20°.

In a second test series, oral surgery patients, after completion of surgery, were tested using the same procedures except that they were requested to record pain intensity and pain relief levels at 30 minutes and then at each hour for the next six hours. The test scores are therefore the sum of seven readings rather than five readings as in the first test. In the tests, the patients were given a placebo, 200 milligrams of fenoprofen calcium, 100 mg of hydroxyzine pamoate or a mixture of 100 mg of hydroxyzine pamoate with 200 mg of fenoprofen calcium. The test data are shown in Table 2 below.

TABLE 2

|  | Placebo | Hydroxyzine Pamoate 100 mg | Fenoprofen Calcium 200 mg | Hydroxyzine Pamoate 100 mg. + Fenoprofen Calcium 200 mg. |
|---|---|---|---|---|
| Number of Patients | 9 | 11 | 11 | 10 |
| Mean Sum Pain Intensity Difference Score | 1.56 | 1.50 | 3.55 | 9.60 |
| Mean Sum Pain Relief Score | 8.33 | 3.25 | 12.00 | 18.40 |

Thus the above tests indicate a synergism of the potentiating kind for the combination of active agent (a) with an active agent (b), and that the combination is thus indicated as particularly useful in alleviating pain. They also confirm that hydroxyzine alone is inactive orally as an analgesic.

As will be appreciated, the precise dose of the NSAID component (a) will also vary depending upon the particular NSAID or NSAIDs to be used. Preferably, the dose will be within the range generally accepted as suitable for practical use in relieving pain when used alone. When two or more NSAIDs will be used to constitute component (a), a lesser amount of each within the practical range will be preferably employed. In general, the invention is practiced using a single NSAID as the component (a). As will be appreciated, the invention may be utilized to obtain pain relief with well reduced amounts of component (a). For example, a per dose range of from 50 to 800 milligrams of Ibuprofen may be utilized even though a generally preferred range of Ibuprofen is from 150 to 600 milligrams.

In Table I, below, there are given various NSAIDs of particular interest along with general (a), preferred (b) and in some cases more preferred (c) milligram dose ranges for each administration (column A); the weight ratio thereto of hydroxyzine when the hydroxyzine dose to be administered is within the range of 25 to 100 mg (Column B); and the weight ratio thereto of hydroxyzine when the hydroxyzine dose to be administered is within the range of 50 to 100 mg (Column C).

TABLE I

|  |  | Column A NSAID dose range | Column B Weight ratio hydroxyzine range at 25–100 mg to NSAID dose range | Column C Weight ratio hydroxyzine range at 50–100 mg to NSAID dose range |
|---|---|---|---|---|
| NSAID Ibuprofen | (a) | 100–800 | 1:32 to 1:1 | 1:16 to 1:1 |
|  | (b) | 150–600 | 1:24 to 1:1.5 | 1:12 to 1:1.5 |
|  | (c) | 200–400 | 1:16 to 1:2 | 1:8 to 1:2 |
| Oxaprozin | (a) | 300–1200 | 1:48 to 1:3 | 1:24 to 1:3 |
|  | (b) | 400–800 | 1:32 to 1:4 | 1:16 to 1:4 |
| Carprofen | (a) | 50–400 | 1:16 to 1:0.5 | 1:8 to 1:0.5 |
|  | (b) | 100–300 | 1:12 to 1:1 | 1:6 to 1:1 |
| Fenoprofen or Fenoprofen calcium | (a) | 50–600 | 1:24 to 1:0.5 | 1:12 to 1:0.5 |
|  | (b) | 100–400 | 1:16 to 1:1 | 1:8 to 1:1 |
|  | (c) | 150–300 | 1:12 to 1:1.5 | 1:6 to 1:1.5 |
| Naproxen or Naproxen sodium | (a) | 100–600 | 1:24 to 1:1 | 1:12 to 1:1 |
|  | (b) | 200–400 | 1:16 to 1:2 | 1:8 to 1:2 |
| Indoprofen | (a) | 25–200 | 1:8 to 1:0.25 | 1:4 to 1:0.25 |
|  | (b) | 50–150 | 1:6 to 1:0.5 | 1:3 to 1:0.5 |
| Ketoprofen | (a) | 25–300 | 1:12 to 1:0.25 | 1:6 to 1:0.25 |
| Flurbiprofen | (b) | 50–200 | 1:8 to 1:0.5 | 1:4 to 1:0.5 |
|  | (a) | 15–200 | 1:8 to 1:0.15 | 1:4 to 1:0.15 |
|  | (b) | 25–150 | 1:6 to 1:0.25 | 1:3 to 1:0.25 |
| Zomepirac | (a) | 15–200 | 1:4 to 1:0.15 | 1:2 to 1:0.15 |
|  | (b) | 25–100 | 1:4 to 1:0.25 | 1:2 to 1:0.25 |
| Piroxicam | (a) | 10–50 | 1:2 to 1:0.1 | 1:1 to 1:0.1 |
|  | (b) | 15–37.5 | 1:1.5 to 1:0.15 | 1:0.75 to 1:0.15 |
| Diflunisal | (a) | 125–1000 | 1:40 to 1:1.25 | 1:20 to 1:1.25 |
|  | (b) | 250–750 | 1:30 to 1:2.5 | 1:15 to 1:2.5 |
| Proquazone | (a) | 60–300 | 1:12 to 1:0.6 | 1:6 to 1:0.6 |
|  | (b) | 75–150 | 1:6 to 1:0.75 | 1:3 to 1:0.75 |
| Aspirin | (a) | 200–1300 | 1:52 to 1:2 | 1:26 to 1:2 |
|  | (b) | 300–650 | 1:26 to 1:3 | 1:13 to 1:3 |
| Tolmetin or Tolmetin sodium | (a) | 300–800 | 1:32 to 1:3 | 1:16 to 1:3 |
|  | (b) | 400–600 | 1:24 to 1:4 | 1:12 to 1:4 |

The limits of weight ratio ranges of hydroxyzine for the hydroxyzine dose ranges of 25 to 120 mg and 70 to 100 mg, to the dose ranges from NSAIDs given in Table I may be readily calculated from the dose ranges given in Column A of Table I for the particular NSAID and such weight ratio ranges are also deemed disclosed herein. It will be evident that the weight ratio ranges of hydroxyzine to the NSAID as indicated above may be used to formulate pharmaceutical compositions in accordance with the invention, provided that a NSAID pain relieving potentiating effective amount of hydroxyzine is included.

The pharmaceutical compositions according to the invention suitably contain pharmaceutically acceptable carriers which are admixed with the active agent components (a) and (b). Such compositions may be prepared from conventional, materials by procedures well known in the art. The compositions of this invention may be adapted for oral administration and administration through the rectum. Forms suitable for oral administration are for example tablets, dispersible powders, granules, capsules, syrups, elixirs or suspensions. Compositions for oral use contain one or more conventional adjuvants, such as sweetening agents flavoring agents, coloring agents and preserving agents, in order to provide an elegant and palatable preparation. Tablets may contain the active ingredients in admixture with conventional pharmaceutically acceptable excipients, e.g. inert carriers, such as calcium carbonate, sodium carbonate, lactose, and talc, granulating and disintegrating agents, e.g. starch and algininic acid, binding agents, e.g. starch gelatin and acacia, and lubricating agents, e.g. magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredients in admixture with any of the conventional excipients utilized in the preparation of such compositions, e.g. suspending agents such as methyl-cellulose, tragacanth and sodium alginate;

wetting agents such as lecithin, polyoxyethylene stearate and polyoxyethylene sorbitan monooleate; and preservatives such as ethyl p-hydroxybenzoate. Capsules may contain the active ingredients alone or admixed with an inert solid carrier, e.g. calcium carbonate, calcium phosphate and kaolin. These pharmaceutical compositions may contain up to about 90% of the active ingredients in combination with the carrier or adjuvant. Preferably the compositions are put up in unit dosage form particularly in unit dosage form for oral administration, e.g. tablets or capsules. Such forms may contain the active ingredients separately, e.g. in separate layers in a layer or mantle tablet or in split capsules. Oral administration is preferred.

Conveniently the active agents will be administered in fixed combinations having e.g. the individual dosages outlined above and in unit dosage form.

They can be administered e.g. in sustained release form or in divided doses 2 to 4 times a day or as indicated by the condition to be treated e.g. 3 to 6 times as needed to relieve pain.

The active agents (a) and (b) can also be administered in the indicated dosages individually and concomitantly.

The following Examples are illustrative of compositions for use in the invention.

EXAMPLE A

A No. 1 capsule containing the ingredients indicated below may be prepared by conventional techniques and administered at a dose of 1 or 2 capsules 4 to 6 times a day to relieve pain.

| Ingredient | Weight (mg) |
| --- | --- |
| Ibuprofen | 200 |
| Hydroxyzine pamoate | 50 |
| Corn starch | 150 |
| Magnesium stearate | 2 |

Three single dose capsules containing 200 mg. of Ibuprofen and 25, 50 and 100 mg. of hydroxyzine hydrochloride respectively and formulated as in Example A, above, are administered in separate clinical oral surgery tests as described above (using a placebo and similar capsules containing the individual ingredients at the above indicated strengths as controls), with the result that after 6 hours a clear potentiation of the pain relieving effects of Ibuprofen by the hydroxyzine is indicated with each such combination.

EXAMPLE B

A tablet containing the ingredients indicated below may be prepared by conventional techniques and administered at a dose of 1 or 2 tablets 3 to 5 times a day to relieve pain.

| Ingredient | Weight (mg) |
| --- | --- |
| Proquazone (micronized) | 75 |
| Hydroxyzine hydrochloride | 25, 50, 75 or 100 |
| Lactose powder | 279.2 |
| Alginic acid | 90 |
| Yellow iron oxide (T-1624) | 1.5 |
| Celloidal silicon dioxide | 13 |

-continued

| Ingredient | Weight (mg) |
| --- | --- |
| Pluronic F-68 | 1.3 |
| Poridone | 10 |
| Stearic acid | 5 |

Three single dose tablets containing 25, 50 and 100 mg of hydroxyzine hydrochloride respectively and formulated as in Example B (75 mg of proquazone), are administered in separate clinical oral surgery tests as described above, with the result that after 6 hours a clear potentiation of the pain relieving effects of proquazone by the hydroxyzine is indicated with each such combination.

The co-administration and combination of components (a) and (b) also substantially reduces or eliminates the nausea-causing effects normally associated with NSAIDs and many other combinations involving analgesics.

What is claimed is:

1. A pharmaceutical composition for oral or rectal administration comprising a pharmaceutically acceptable carrier and a pain relieving effective amount of the combination of: (a) one or more arylpropionic acid non-steroidal anti-inflamatory/analgesic agents selected from the group consisting of ibuprofen, suprofen, carprofen, fenoprofen calcium, naproxen, naproxen sodium, indoprofen, ketoprofen and flurbiprofen; and (b) hydroxyzine or an acid salt form thereof in an amount sufficient to potentiate the analgesic action of component (a).

2. A composition of claim 1 in which component (a) is ibuprofen or fenoprofen calcium.

3. A composition of claim 1 in tablet or capsule unit dosage form.

4. A composition in accord with claim 1 in which the component (a) is present in at least an amount which by itself would be minimally effective clinically to produce analgesia in the adult human.

5. A composition in accord with claim 4 in which component (a) is ibuprofen and in which the weight ratio of component (b) to ibuprofen is within the range of from 1:32 to 1:1.

6. A composition in accord with claim 5 in which the weight ratio of component (b) to ibuprofen is within the range of from 1:24 to 1:1.5.

7. A composition in accord with claim 5 in which the weight ratio of component (b) to ibuprofen is within the range of from 1:8 to 1:2.

8. A composition in accord with claim 4 in which component (a) is fenoprofen calcium and in which the weight ratio of component (b) to component (a) is within the range of from 1:24 to 1:0.5.

9. A composition in accord with claim 8 in which the weight ratio of component (b) to component (a) is within the range of from 1:16 to 1:1.

10. A composition in accord with claim 8 in which the weight ratio of component (b) to component (a) is within the range of from 1:6 to 1:1.5.

11. A composition in accord with claim 1 in which the component (b) is present in an amount of from 25 to 100 milligrams.

12. A composition in accord with claim 5 in which the component (b) is present in an amount of from 25 to 100 milligrams.

13. A composition in accord with claim 8 in which the component (b) is present in an amount of from 25 to 100 milligrams.

14. A composition in accord with claim 3 in which the component (b) is present in an amount of from 50 to 100 milligrams and component (a) is present in an amount from 100 to 400 milligrams.

15. A composition in accord with claim 10 in which the component (b) is present in an amount of from 50 to 100 milligrams and component (a) is present in an amount from 150 to 300 milligrams.

16. A composition in accord with claim 4 in which the component (b) is present in an amount of from 25 to 100 milligrams.

17. A composition in accord with claim 4 in which the component (b) is present in an amount of from 50 to 100 milligrams.

18. The method of relieving pain in a human subject comprising orally or rectally co-administering to said subject; (a) one or more arylpropionic acid non-steroidal anti-inflammatory/analgesic agents selected from the group consisting of ibuprofen, suprofen, carprofen, fenoprofen calcium, naproxen, naproxen sodium, indoprofen, ketoprofen and flurbiprofen; and (b) hydroxyzine or an acid salt form thereof in an amount sufficient to potentiate the analgesic action of component (a); said components (a) and (b) being co-administered in a total pain relieving effective amount.

19. The method of claim 18 in which component (a) is ibuprofen or fenoprofen calcium.

20. The method of claim 18 in which the component (a) is administered in at least an amount which by itself would be minimally effective clinically to produce analgesia in the adult human.

21. The method of claim 20 in which component (a) is ibuprofen and in which the weight ratio of component (b) to ibuprofen is within the range of from 1:32 to 1:1.

22. The method of claim 21 in which the weight ratio of component (b) is within the range of from 1:24 to 1:1.5.

23. The method of claim 21 in which the weight ratio of component (b) to ibuprofen is within the range of from 1:8 to 1:2.

24. The method of claim 20 in which component (a) is fenoprofen calcium and in which the weight ratio of component (b) to component (a) is within the range of from 1:24 to 1:0.5.

25. The method of claim 24 in which the weight ratio of component (b) to component (a) is within the range of from 1:16 to 1:1.

26. The method of claim 24 in which the weight ratio of component (b) to component (a) is within the range of from 1:6 to 1:1.5.

27. The method of claim 18 in which the component (b) is administered in an amount of from 25 to 100 milligrams.

28. The method of claim 21 in which the component (b) is administered in an amount of from 25 to 100 milligrams.

29. The method of claim 24 in which the component (b) is administered in an amount of from 25 to 100 milligrams.

30. The method of claim 23 in which the component (b) is administered in an amount of from 50 to 100 milligrams and component (a) is administered in an amount from 100 to 400 milligrams.

31. The method of claim 27 in which the component (b) is administered in an amount of from 50 to 100 milligrams and component (a) is administered in an amount from 150 to 300 milligrams.

32. The method of claim 20 in which the component (b) is administered in an amount of from 25 to 100 milligrams.

33. The method of claim 20 in which the component (b) is administered in an amount of from 50 to 100 milligrams.

34. The method of claim 30 in which component (b) is present in an amount of from 70 to 100 milligrams.

* * * * *